(12) United States Patent
Felix et al.

(10) Patent No.: US 11,000,663 B2
(45) Date of Patent: May 11, 2021

(54) INTRA-MOULD SUBSTRATE

(71) Applicant: Fisher & Paykel Healthcare Limited, Auckland (NZ)

(72) Inventors: David Monroy Felix, Auckland (NZ); Vitaly Kapelevich, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 323 days.

(21) Appl. No.: 16/085,323

(22) PCT Filed: Mar. 16, 2017

(86) PCT No.: PCT/IB2017/051521
§ 371 (c)(1),
(2) Date: Sep. 14, 2018

(87) PCT Pub. No.: WO2017/158543
PCT Pub. Date: Sep. 21, 2017

(65) Prior Publication Data
US 2019/0117926 A1    Apr. 25, 2019

Related U.S. Application Data

(60) Provisional application No. 62/309,405, filed on Mar. 16, 2016.

(51) Int. Cl.
*A61M 16/06*    (2006.01)
*A62B 18/08*    (2006.01)

(52) U.S. Cl.
CPC ....... *A61M 16/0683* (2013.01); *A62B 18/084* (2013.01); *A61M 16/0633* (2014.02); *A61M 2207/00* (2013.01); *A61M 2210/0618* (2013.01)

(58) Field of Classification Search
CPC ...... A61M 16/0683; A61M 2210/0618; A61M 16/0633; A61M 2207/00; A61M 16/0488;
(Continued)

(56) References Cited

U.S. PATENT DOCUMENTS

2005/0262619 A1* 12/2005 Musal ................... A42B 3/145
2/421
2012/0247490 A1   10/2012 Matthews
2016/0074614 A1   3/2016 Huddart et al.

FOREIGN PATENT DOCUMENTS

CA      2995960 A1 *  2/2017  ........... A62B 18/025
WO  WO 2009/148956     12/2009
(Continued)

OTHER PUBLICATIONS

European Search Report; EP Application No. 17765962.0; dated Oct. 11, 2019; 8 pages.
(Continued)

*Primary Examiner* — Kendra D Carter
*Assistant Examiner* — Arielle Wolff
(74) *Attorney, Agent, or Firm* — Knobbe, Martens, Olson & Bear, LLP

(57) ABSTRACT

A headgear portion or assembly for use in combination with a breathing apparatus in some configurations is at least substantially inelastic and is three dimensional in shape. The headgear portion or assembly can comprise a plastic core, a substrate and a textile casing. The substrate and textile casing have retaining structures to attach the textile casings to the substrates and the substrates to each other.

14 Claims, 15 Drawing Sheets

(58) Field of Classification Search
CPC ... A62B 18/084; B63C 11/12; A44B 18/0088;
Y10T 24/45225
See application file for complete search history.

(56) References Cited

FOREIGN PATENT DOCUMENTS

| | | | |
|---|---|---|---|
| WO | WO 2010/066004 | 6/2010 | |
| WO | WO-2010066004 A1 * | 6/2010 | ........ A61M 16/0683 |
| WO | WO 2012/045127 A1 | 4/2012 | |
| WO | WO 2016/043603 A1 | 3/2016 | |
| WO | WO 2017/150990 A1 | 9/2017 | |

OTHER PUBLICATIONS

International Search Report, Application No. PCT/IB2017/051521; 6 pages; dated May 23, 2017.

* cited by examiner

INTRA-MOULD SUBSTRATE

INCORPORATION BY REFERENCE TO PRIORITY APPLICATIONS

This application is a national stage application under 35 U.S.C. § 371(c) of PCT Application No. PCT/IB2017/051521, filed Mar. 16, 2017, which is related to and claims priority from U.S. Provisional Patent Application No. 62/309,405, filed Mar. 16, 2016, the entirety of which is hereby incorporated by reference herein and made a part of the present disclosure.

BACKGROUND

Technical Field

The present disclosure generally relates to headgear for use in combination with a breathing apparatus. More particularly, the present disclosure relates to a system and method for intra-moulding a headgear arrangement having an improved edge finish and improved manufacturability.

Description of the Related Art

The treatment of respiratory ailments or conditions with therapies, such as NIV, Bi-level or CPAP, involves the delivery of pressurized air to the airways of a human via a conduit and a breathing apparatus (e.g., a mask or cannula). Typically, a mask creates at least a substantial "seal" on or around the nose and/or the mouth of a user. The mask is connected to and supported by a headgear arrangement that is worn on the head of the user. The headgear arrangement comprises a series of straps that pass around the back and/or top of a user's head and also which support the mask against the user's nose and/or the mouth.

Headgear arrangements may be formed using an intra-moulding technique as disclosed in U.S. patent application Ser. No. 14/856,502, which is herein incorporated by reference. Accordingly, the headgear arrangements have a plastic core that is surrounded by a textile layer or casing. The headgear arrangements are typically formed by inserting inner and outer textile layers into a molding tool, closing the tool, and injecting plastic between the inner and outer textile layers. Generally, the headgear arrangements have a junction portion where multiple straps intersect and are connected. That is, in the headgear arrangements, the top strap, the rear strap, and the side straps are connected at the junction portion. The junction portion has a substantially triangular profile region with multiple curved segment edges and truncated corners from which straps may extend, in some configurations. As a result of their shape, the junction portions are difficult to manufacture. More specifically, the non-linear shape and geometry of the junction portion makes it difficult to wrap the textile layers around the plastic core because it is difficult to align and secure loose textile layers within a mould tool cavity prior to closing the mould. Further, the inner and outer textile layers may move out of position relative to the mould when the mould tool is closed or can be pushed out of position by the pressure of the injected plastic material. Therefore, it is desirable to provide a headgear strap having a construction that is easier and more reliable to intra-moulded.

SUMMARY

The systems, methods and devices described herein have innovative aspects, no single one of which is indispensable or solely responsible for their desirable attributes. Without limiting the scope of the claims, some of the advantageous features will now be summarized.

In accordance with at least one of the embodiments disclosed herein, a headgear strap for a headgear assembly is disclosed. The headgear strap includes a first substrate, a second substrate attached to the first substrate, a first textile casing attached to the first substrate, a second textile casing attached to the second substrate, and an intra-moulded core positioned between the first and second textile casings. The first and second substrates, the first and second textile casings and the intra-moulded core are formed as an integral structure by the application of a molten plastic material between the first and second textile casings.

According to a further aspect, the first textile casing covers an inwardly-facing surface of the headgear assembly and the second textile casing covers an outwardly-facing the surface of the headgear assembly.

According to a further aspect, the ends of the first and second textile casing are positioned between the first and second substrates.

According to a further aspect, each of the first and second substrates include a first retaining structure, and each of the first and second textile casings include a second retaining structure, wherein the first and second retaining features are configured to engage each other to attach the first textile casing onto the first substrate and the second textile casing onto the second substrate.

According to a further aspect, the first retaining structure of the first substrate engages the first retaining structure of the second substrate to connect the first and second substrates.

According to a further aspect, the first retaining structure includes a post protruding outward from a surface of at least one of the first and second substrates, and a socket positioned on at least an other of the first and second substrates, the socket having an inner hole, wherein the post is positioned within the inner hole to connect the first and second substrates.

According to a further aspect, the socket protrudes outward from a surface of the other of the first and second substrates.

According to a further aspect, the second retaining structure includes at least one hole extending through each of the first and second textile casings, wherein at least one of the post and the socket engages the hole to attach the first textile casing on the first substrate and the second textile casing on the second substrate.

According to a further aspect, the second retaining structure is positioned on portions of the first and second textile casing that are positioned between the first and second substrates.

According to a further aspect, a strap connector is preformed in at least one of the first and second substrates.

According to a further aspect, a length adjustment mechanism is preformed in at least one of the first and second substrates.

According to a further aspect, an angular adjustment mechanism is preformed in at least one of the first and second substrates.

According to a further aspect, at least one of the first and second substrates includes a gate.

According to a further aspect, the first and second substrates are identical.

According to a further aspect, the intra-moulded core comprises an injection moulded plastic material that is injected between the first and second textile casings.

In accordance with at least another of the embodiments disclosed herein, a headgear strap assembly is disclosed. The headgear strap assembly includes a substrate having an outer surface and an inner surface that is opposite the outer surface, and a textile casing overlaid onto the outer surface of the substrate. The textile casing has a width that is greater than a width of the substrate.

According to a further aspect, the textile casing includes an overhanging portion that extends beyond edges of the outer surface of the substrate, and the overhanging portion is configured to be folded over the edges onto the inner surface of the substrate.

According to a further aspect, the substrate includes a first retaining structure, and the textile casing includes a second retaining structure, wherein the first and second retaining features are configured to engage each other to attach the textile casing to the substrate.

According to a further aspect, the first retaining structure includes a post protruding outward from the inner surface of the substrate.

According to a further aspect, the first retaining structure includes a socket protruding outward from the inner surface of the substrate, the socket having an inner hole extending through the socket.

According to a further aspect, the second retaining structure includes at least one hole extending through the textile casing, wherein at least one of the post and the socket engages the hole to attach the textile casing onto the substrate.

According to a further aspect, the second retaining structure is positioned on the overhanging portion of the textile casing.

In accordance with at least another of the embodiments disclosed herein, a method for forming a headgear assembly for a respiratory interface is disclosed. The method includes securing textile casings onto an outer portion of each of a pair of substrates, connecting the pair of substrates along an inner portion of each of the pair of substrates, positioning the pair of substrates within a moulding tool, injecting molten plastic material between the pair of substrates, and allowing the molten plastic material to solidify to form a plastic core between the textile casings.

According to a further aspect, securing the textile casing includes folding the textile casing over ends of each of the pair of substrates such that ends of the textile casing are positioned between the pair of substrates.

According to a further aspect, securing the textile casing includes fastening the ends of the textile casing to the inner portion of each of the pair of substrates.

According to a further aspect, connecting the pair of substrates includes interlocking the inner portions of the pair of substrates.

According to a further aspect, the pair of substrates are preformed unitarily as an integral structure.

According to a further aspect, the pair of substrates and molten plastic material chemically bond to provide a uniform plastic core between the textile casings.

In accordance with at least another of the embodiments disclosed herein, a junction portion in a headgear assembly at which two or more straps of the headgear assembly connect is disclosed. The junction portion includes a first substrate; a second substrate attached to the first substrate; a first textile casing attached to the first substrate; a second textile casing attached to the second substrate; and a plastic core that is surrounded by the first and second textile casings and is bonded to the first and second substrates and the first and second textile casings.

According to a further aspect, the first textile casing covers an inwardly-facing surface of the headgear assembly and the second textile casing covers an outwardly-facing the surface of the headgear assembly.

According to a further aspect, the ends of the first and second textile casing are positioned between the first and second substrates.

According to a further aspect, each of the first and second substrates include a first retaining structure, and each of the first and second textile casings include a second retaining structure, wherein the first and second retaining features are configured to engage each other to attach the first textile casing onto the first substrate and the second textile casing onto the second substrate.

According to a further aspect, the first retaining structure of the first substrate engages the first retaining structure of the second substrate to connect the first and second substrates.

According to a further aspect, the first retaining structure includes a post protruding outward from a surface of at least one of the first and second substrates, and a socket positioned on at least an other of the first and second substrates, the socket having an inner hole, wherein the post is positioned within the inner hole to connect the first and second substrates.

According to a further aspect, the socket protrudes outward from a surface of the other of the first and second substrates.

According to a further aspect, the second retaining structure includes at least one hole extending through each of the first and second textile casings, wherein at least one of the post and the socket engages the hole to attach the first textile casing on the first substrate and the second textile casing on the second substrate.

According to a further aspect, the second retaining structure is positioned on portions of the first and second textile casing that are positioned between the first and second substrates.

According to a further aspect, the junction portion further includes a strap connector preformed in at least one of the first and second substrates.

According to a further aspect, the junction portion further includes a length adjustment mechanism preformed in at least one of the first and second substrates.

According to a further aspect, the junction portion further includes an angular adjustment mechanism preformed in at least one of the first and second substrates.

According to a further aspect, at least one of the first and second substrates includes a gate.

According to a further aspect, the first and second substrates are identical.

According to a further aspect, the plastic core comprises an injection moulded plastic material that is injected between the first and second textile casings.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION OF THE PREFERRED EMBODIMENT

Figure 1A:
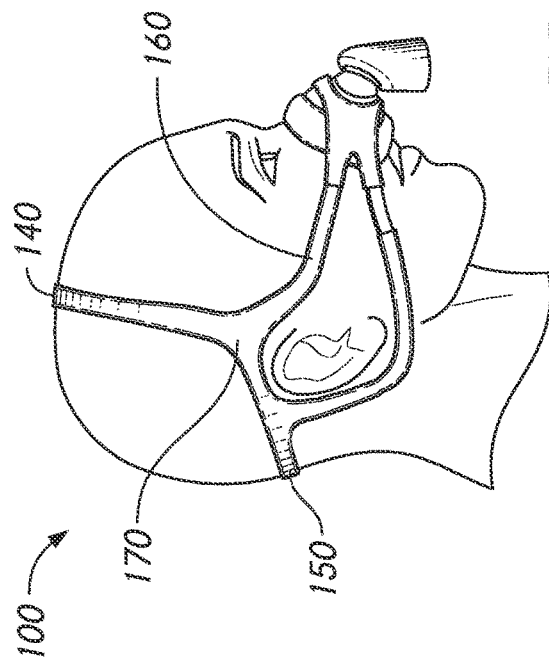
FIG. 1A illustrates a side view of a headgear arrangement formed by the intra-moulding arrangement of the present disclosure.
Figure 1C:
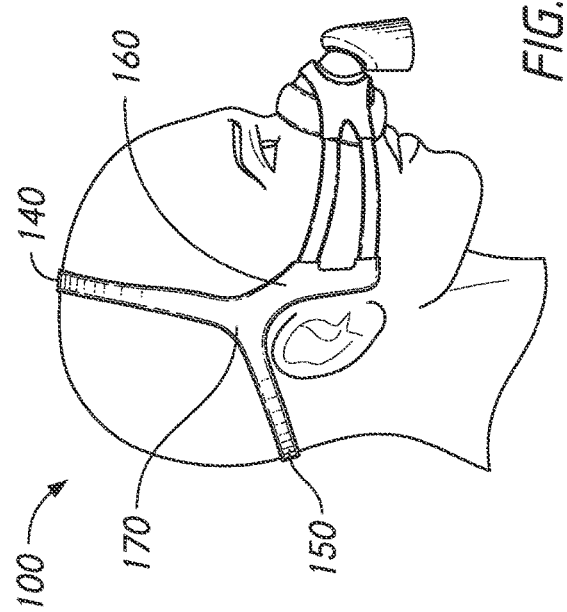
FIG. 1C illustrates a side view of another alternative headgear arrangement formed by the intra-moulding arrangement of the present disclosure.
Figure 1B:
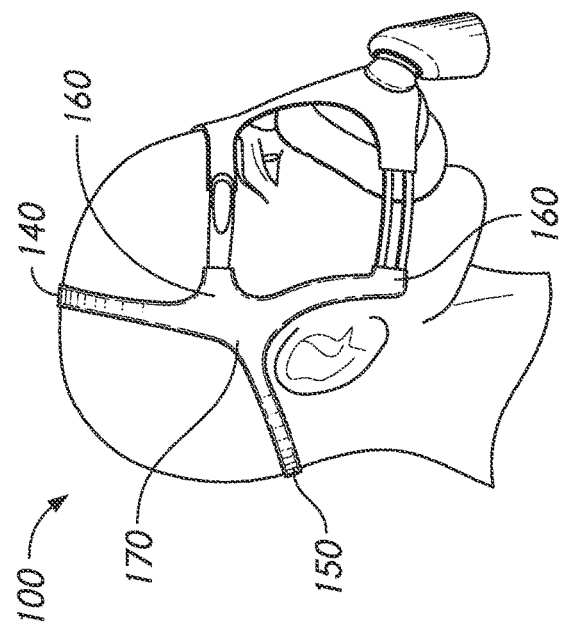
FIG. 1B illustrates a side view of an alternative headgear arrangement formed by the intra-moulding arrangement of the present disclosure.
Figure 1D:
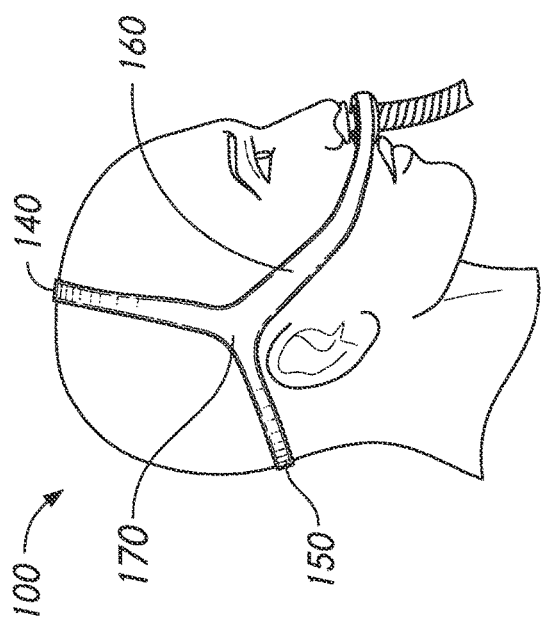
FIG. 1D illustrates a side view of a further alternative headgear arrangement formed by the intra-moulding arrangement of the present disclosure.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

As used herein the term 'substantially inelastic' shall refer to the ability of a headgear or material to resist stretching relative to the loads to which it may be subjected. Thus, a headgear or material may be substantially inelastic in one direction and may be somewhat elastic in another direction. In some configurations, the headgear or material is configured to be substantially inelastic in a direction in which loads are applied by therapy with which the headgear or material is intended for use. A substantially inelastic headgear or material, for example, can resist stretching that would compromise a seal of a respiratory mask in a sealed system under normal or expected conditions. In an unsealed system, a substantially inelastic headgear or material, for example, can resist stretching that would compromise the appropriate placement of the respiratory interface in response to normal or expected conditions, such as hose pull forces or movement of the user. When the expected loading forces are relatively low, the headgear or material may have greater elasticity because the load will not be sufficient to cause stretching. Conversely, if it is expected that the headgear and/or material will be subjected to high loading forces, then greater inelasticity will be required to resist stretching.

FIGS. 1A to 1D show non-limiting exemplary embodiments of headgear arrangements of the present disclosure in use in combination with a breathing apparatus 110. The headgears 100 are configured to be substantially inelastic and three-dimensional (3D) in structure. As used herein, a three-dimensional structure is one that does not lie in a single plane, but is shaped to extend in multiple planes. In other words, the three-dimensional structure is not flat. The illustrated headgears 100 comprise a right side and a left side. Only the right side is illustrated in the Figures but the right and left sides are substantially identical. The right and left sides are formed as substantially two dimensional (2D) pieces, i.e., they are formed in a flat structure. The right and left sides each include a top strap 140, a rear strap 150, a front strap 160, and a yoke or junction portion 170. When the top straps 140 and the rear straps 150 of the right and left sides are joined together, a 3D bifurcated structure is formed.

The top strap 140 is configured to extend upwardly from the junction portion 170 at a location generally above each ear of the user and over the parietal or frontal region of a user's head. The rear straps 150 comprise an elongate member and are configured to extend rearward from the junction portion 170 from a location generally above each ear of the user and around the occipital region of the user's head. The rear strap 150 is configured to be positioned at or near a central point or location on the rear of the user's head. The rear strap 150 is configured to directly or indirectly adjoin the junction portion 170. The front strap 160 comprises elongate members that are configured to directly or indirectly adjoin the junction portion 170 and extend forward across the user's temples towards their nose. In some configurations, the front strap 160 is shorter than one or both of the top strap 140 or the rear strap 150.

In some configurations, the junction portion 170 comprises a relatively triangular section that is configured to provide a lateral junction between the corresponding top strap 140, rear strap 150 and front strap 160. Each of the top, rear and front straps 140, 150, 160 is adjoined directly or indirectly to the junction portion 170 in a continuous manner such that the right and left sides of the headgear 100 are formed as unitary pieces. The thickness and/or shape of the junction portion 170 can be defined to restrict rotational movement about a lateral axis or axis extending in a thickness direction of the junction portion 170 of the top, rear and front straps 140, 150, 160 relative to each other. Such an arrangement can provide the breathing apparatus with greater stability on the user's face.

Figure 2A:
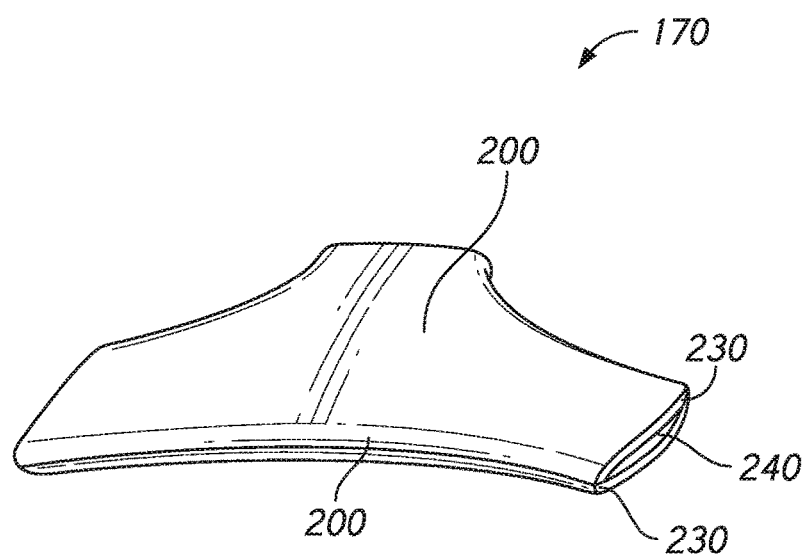
FIG. 2A illustrates a top perspective view of a junction portion of a headgear formed by the intra-moulding arrangement of the present disclosure.

FIG. 2A illustrates the junction portion 170 of the headgear 100 without the top, rear and front straps attached. For the purpose of discussion, the following disclosure is focused on the forming of the junction portion 170. However, the configuration and construction of the junction portion 170 disclosed herein may be used to form other portions of the headgear 100 such as the straps, alone or in combination with the junction portion. The following disclosure also focuses on forming the junction portion 170 because the junction portion has a non-linear shape and geometry which makes the junction portion 170 difficult to manufacture. As shown in FIG. 2A, the junction portion 170 comprises a substantially triangular profile region with multiple curved segment and truncated corners from which the top, rear and front straps extend. The junction portion 170 has a layered composition comprising a plastic core 240 surrounded by a first textile casing 200 and a second textile casing 200. The first and second textile casings 200 comprise layers of textile material. The first textile casing 200 is configured to contact the user's head while the second textile casing 200 is configured to face away from the user's head, or vice versa. The first and second textile casings 200 may be made from the same or different textiles and can be configured to provide a soft and, in some embodiments, cushioned covering for the core 240. However, in at least some preferred embodiments, the core 240 forms the primary structure of the headgear 100 and the textile casings 200 are utilized to provide the headgear 100 with a softer texture, improved moisture wicking properties and/or increased friction with the user's face relative to a headgear having the core 240 but without the casings 200. Such an arrangement is in contrast to headgear arrangements constructed primarily of an elastic or flexible material that utilize localized rigidizing structures.

In some configurations, the core 240 comprises a relatively rectangular cross-section of a thermoform or thermoset plastic material that is configured to provide the headgear 100 with the aforementioned 3D structure. The core 240 provides the foundation for the overall structure of the headgear 100. The plastic composition of the core 240 offers the benefits of a resilient structure that is capable of maintaining a preformed shape while conforming somewhat to the individual cranial geometry of the user. The shape and geometry of the core 240 in combination with the material selection allows the headgear 100 to be flexible in a horizontal direction across the user's face and relatively inflexible in a vertical direction across the user's face. This flexibility in one direction allows the headgear 100 to conform to a user's head while providing rigidity in a direction that stabilizes and minimizes dislodging of the mask or seal on a user's face.

In some configurations, the first and second textile casings 200 are configured to be permanently bonded to the core 240 such that the core 240 is completely encased and the headgear 100 is formed from composite material. The first and second textile casings 200 are held together in close proximity by their bonds with the core 240. As shown in FIG. 2A, each of the first and second textile casings 200 have a folded-over edge 230 along their outer perimeters. As will be discussed in detail below, the ends of the first and second textile casings 200 are folded inward into and toward an inner cavity formed by the first and second textile casings 200. The first and second textile casings 200 contact each other at their folded-over edges 230. In some configurations, the first and second textile casings 200 do not directly contact each other at their folded-over edges 230. That is, the folded-over edges 230 can be separated from one another such that a portion of the core 240 is left exposed. In other configurations, the folded-over edge 230 may be skewed towards one or other of the first and second textile casings 200.

Figure 2B:
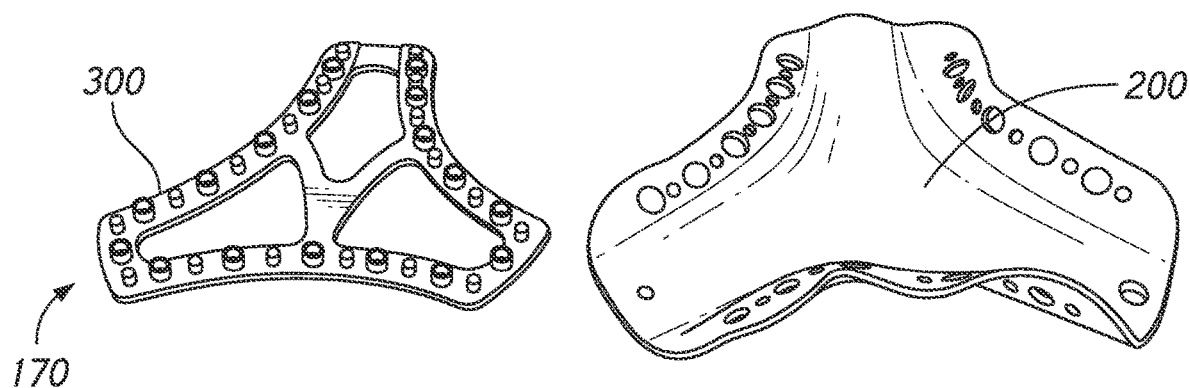
FIG. 2B illustrates a top perspective view of a textile casing and a substrate for forming the junction portion of FIG. 2A.

FIG. 2B shows the components comprising one-half or one side of the junction portion 170 (i.e., an inward-facing portion or an outward-facing portion of the junction portion 170) prior to assembly and intra-moulding. As shown, the junction portion 170 comprises a textile casing 200 and a plastic substrate 300. Accordingly, in the illustrated configuration, the junction portion 170 is formed as an intra-moulded component using a pair of textile casing 200 and a pair of substrates 300. That is, in the illustrated configuration, the junction portion 170 is formed by joining a pair of substrates 300 that have a textile casing 200 attached to their outer surfaces. Further, the substrate 300 is configured to support and secure the textile casing 200 within a mould tool before intra-moulding. That is, the substrate 300 forms a frame structure that the textile casing 200 is wrapped over and secured to. Securing the textile casings 200 to the substrates 300 prevents or inhibits the textile casings 200 from moving out of position or alignment when the mould tool is closed. Further, securing the textile casings 200 to the substrates 300 prevent or inhibits the textile casings 200 from being pushed out of place by the pressure of the injected material during the intra-moulding process. The textile casing 200 and the substrate 300 have a substantially similar shape and geometry. In the illustrated configuration, the substrate 300 is centered or positioned within a center of the textile casing 200 such that the outer edges of the substrate 300 are substantially equidistant from the outer edges of the textile casing 200.

Headgear arrangements may be formed using an intra-moulding technique as disclosed in U.S. patent application Ser. No. 14/856,502, which is herein incorporated by reference. "Intra-moulding" comprises forming a component as a plastic core and a textile casing as an integral structure by the application of molten plastic into the textile casing. A strap or any other component that has been "intra-moulded" is a component formed by the application of molten plastic into the textile casing. Throughout this specification, reference is made to "intra-moulding", processes, techniques, arrangements and components made by such moulding, processes and techniques. It is to be appreciated that all such references are general references to embodiments of the present disclosure and are not intended to be specifically limiting.

Figure 3A:
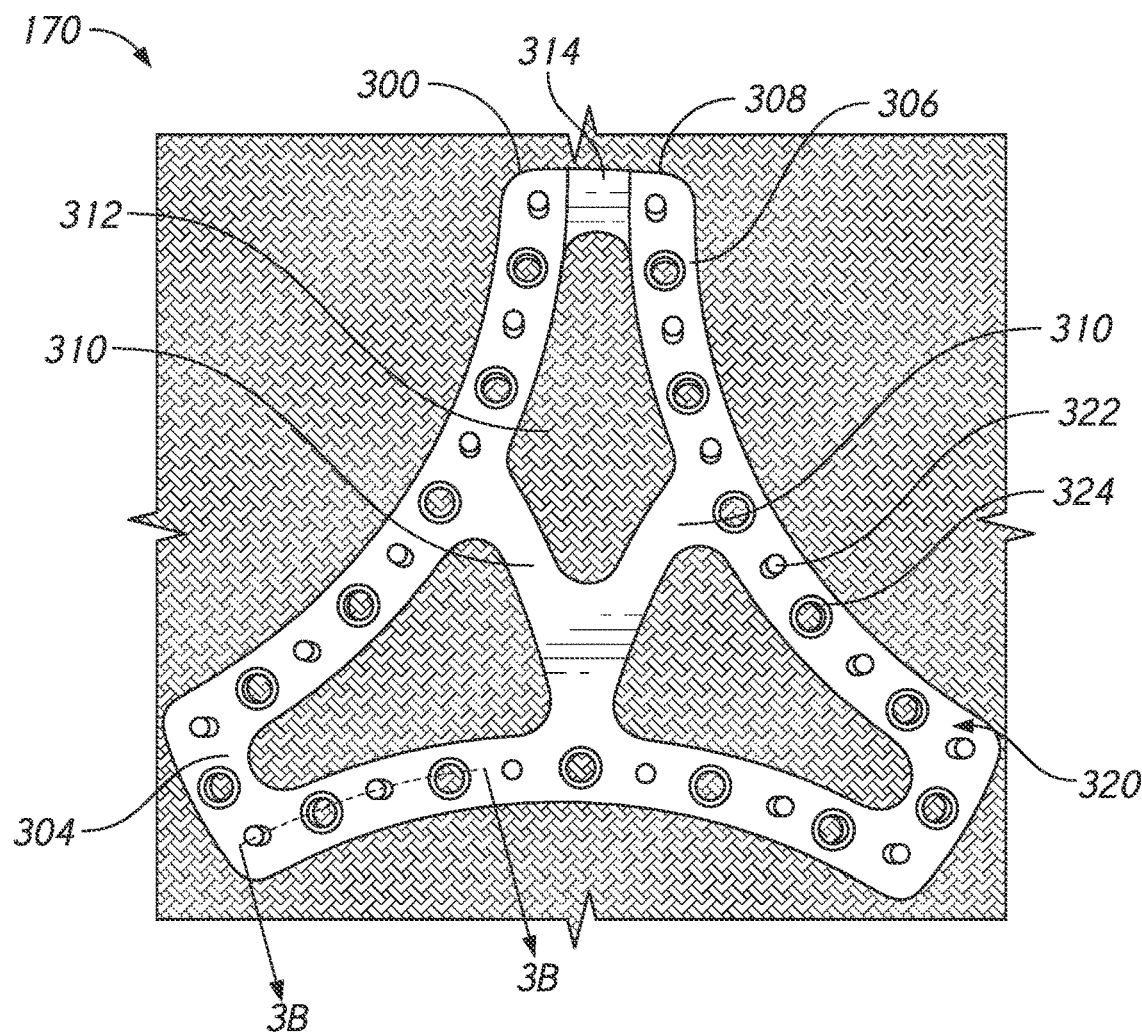
FIG. 3A illustrates a top view of the substrate.

FIG. 3A illustrates a top view of the substrate 300. The illustrated substrate 300 has a triangular shape having curved portions 306 connected to end portions 308. In some configurations, the end portions 308 serve as mounting points where the top, rear and front straps may be attached to, bonded to, or integrally formed with the substrate 300. The substrate 300 is substantially flat and planar having an outer surface 302 and an inner surface 304. As will be discussed further below, the outer surface 302 faces the textile casing 200 and the inner surface 304 faces an opposing and adjoining substrate 300. Although the substrate 300 is illustrated as substantially flat and planar, it should be understood to one of ordinary skill in the art that the substrate 300 may have a contoured three-dimensional shape. The substrate 300 is made from a substantially inelastic material, such as polypropylene or nylon, for example but without limitation. In embodiments where the headgear 100 is expected be subjected to low loading forces, the substrate 300 may be made of other materials, such as, but not limited to, thermoplastic elastomers (TPE) or silicone. In some embodiments, the substrate 300 may have a degree of elasticity and one or both of the inner and/or outer textile casings 200 can be substantially inelastic. Further, in some configurations, the substrates 300 may differ in shape, geometry, material, and/or material properties. That is, the invention is not limited to substrates having identical features and characteristics.

The substrate 300 forms a frame or skeleton structure for the junction portion 170. The substrate 300 has crossbars 310 connected to each other and to the midpoints of the curved portions 306. The crossbars 310 structurally connect the curved portions 306 to strengthen the substrate 300 and prevent the substrate 300 from yielding due to forces applied by the top, rear and front straps. Further, the crossbars 310 prevent the curved portions 306 of the substrate 300 from collapsing and/or distorting when the textile casing 200 is wrapped over the substrate 300. The substrate 300 has apertures 312 defined by the curved portions 306 and the crossbars 310. The apertures 312 allow the substrate 300 to be thinner and thus the headgear to be lighter and less bulky while the crossbars 310 provide strength and stability to the curved portions 306. The apertures 312 also provide gaps for core material to fill during the intra-moulding process. The core material may be injected into the junction portion 170 through a gate 314 positioned on an end portion 308. The gate 314 is recessed into the substrate 300 and extends toward the apertures 312.

Figure 3B:
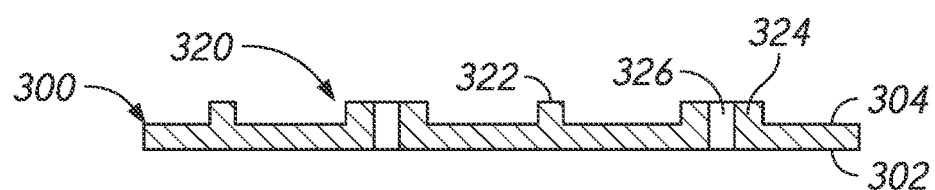
FIG. 3B illustrates a cross-sectional view of the substrate along a line 3B-3B in FIG. 3A.

The substrate 300 has a plurality of textile retaining features 320 positioned along the curved portions 306 and end portions 308. As will be discussed in greater detail below, the textile retaining features 320 on the substrate 300 engage the substrate retaining features 220 on the textile casing 200 to secure the textile casing 200 to the substrate 300. As shown in FIG. 3B, the textile retaining features 320 protrude from the inner surface 304 of the substrate 300 and comprise a plurality of posts 322 and sockets 324 in alternating arrangement that are equidistantly spaced along the curved portions 306 and the end portions 308. The posts 322 and sockets 324 may have their centers aligned on a centerline and the centerline may be positioned along a median of the curved portions 306 and end portions 308 (i.e., equidistant between the edges of the curved portions 306 and end portions 308). It should be understood to one of ordinary skill in the art that the posts 322 and sockets 324 are not limited to having their centers aligned on a centerline and may have their centers positioned at varying locations on the curved portions 306 connected to end portions 308.

The posts 322 and sockets 324 are cylindrical in shape and circular in cross-section. The posts 322 are illustrated as solid cylindrical columns that protrude perpendicularly outward from the inner surface 304 of the substrate 300. The sockets 324 are illustrated as hollow cylindrical tubes that also protrude perpendicularly outward from the inner surface 304 of the substrate 300. The sockets 324 have an interior hole 326 that extends through the socket 324 and, in some configurations, also through the substrate 300. In other words, in some configurations, the interior hole 326 does not penetrate or extend through the entire substrate 300. The posts 322 have an outer diameter that is similar to the diameter of the interior hole 326 (i.e., the inner diameter of the socket 324). As such, the post 322 and socket 324 may have a snap fit or interference fit to retain the post 322 in the socket 324 when connected. The thickness of the walls of the socket 324 (i.e., the difference between the diameter of the interior hole 326 and outer diameter of the socket 324) may be similar to a thickness of the substrate 300.

In some configurations, the sockets 324 may comprise only of holes 326 that extend through the thickness of the substrate 300. That is, the sockets 324 have holes 326 that are recessed into the inner surface 304 of the substrate 300 but do not have a hollow cylindrical tube that protrudes perpendicularly outward from the inner surface 304 of the substrate 300. Such an arrangement may provide a thinner headgear, as the pair of substrates 300 will only be separated by the thickness of the textile casings 200. A thinner headgear may be desirable for aesthetics and user comfort and perception.

The junction portion 170 is formed by connecting together a pair of substrates 300 prior to intra-moulding. That is, when connecting a substrate 300 to an adjoining substrate 300, the posts 322 of the substrate 300 are inserted into and engage the sockets 324 of the adjoining substrate 300. Accordingly, the adjoining substrate 300 also has a plurality of alternating posts 322 and sockets 324 that are equidistantly spaced along the curved portions 306 and the end portions 308. However, in the illustrated arrangement, the order of the posts 322 and sockets 324 on the adjoining substrate 300 may be inversed, reversed or offset such that a socket 324 is positioned at a position on the adjoining substrate 300 to receive a post 322 of the substrate 300 (i.e., in contrast to having two opposing posts 322 or two opposing sockets 324). Put another way, the adjoining substrate 300 may have an opposite pattern of posts 322 and sockets 324 such that the posts 322 of the adjoining substrate 300 align with the sockets 324 of the other substrate, and vice versa. In some configurations (not shown), one substrate 300 may have only posts 322 while the adjoining substrate 300 has only sockets 324.

Figure 4:
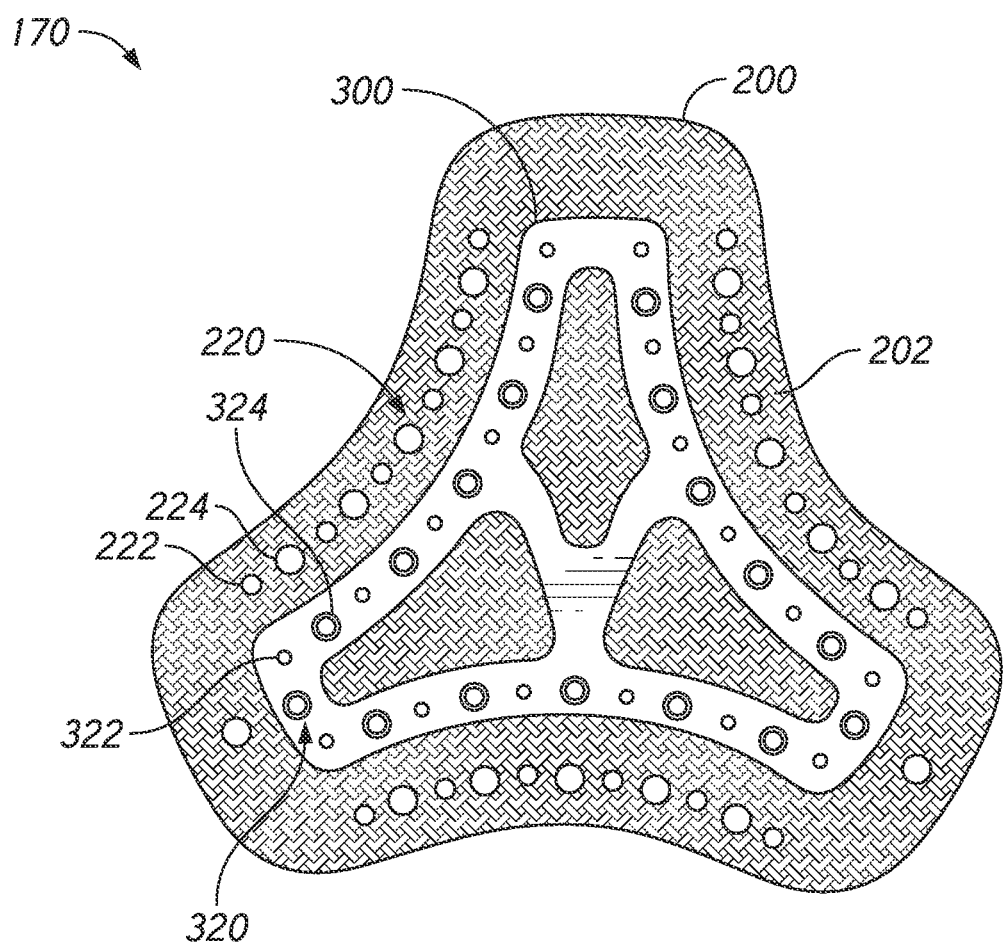
FIG. 4 illustrates a top view of the substrate overlaid onto the textile casing.
Figure 5A:
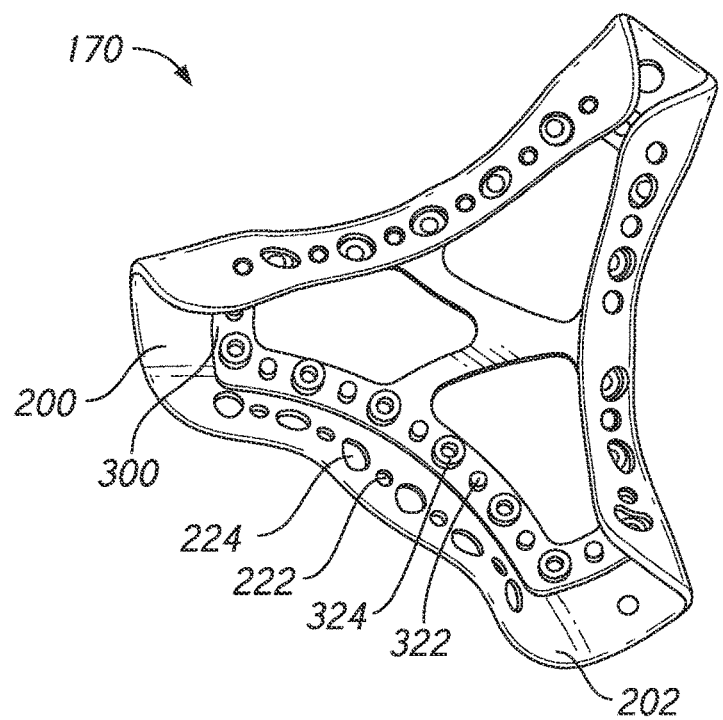
FIG. 5A illustrates a top view of the textile casing being folded over the substrate.
Figure 5B:
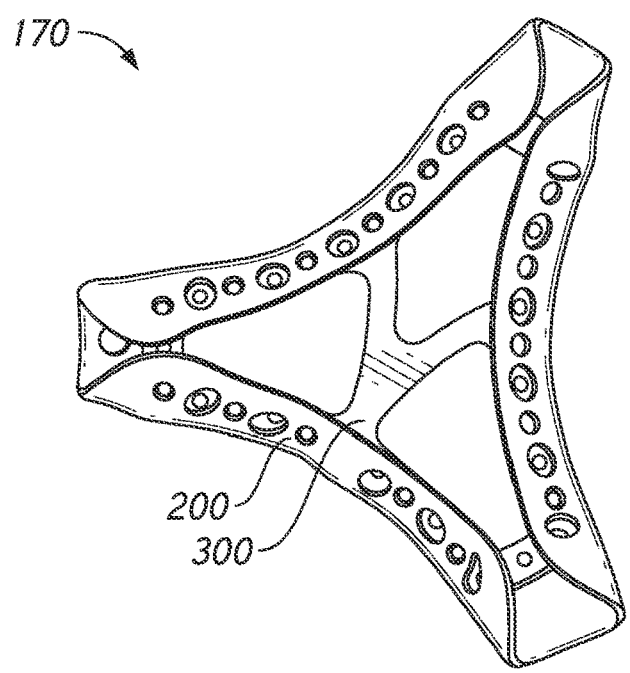
FIG. 5B illustrates a top view of the textile casing entirely folded over the substrate.

FIG. 4 illustrates the textile casing 200 with a substrate 300 overlaid. The textile casing 300 can be made of any suitable textile, such as microfiber towelling, suede, or unbroken loop (UBL). The textile casing 200 has substantially the same shape as the substrate 300 but the textile casing 200 is larger (i.e., longer, wider) such that the outer edges of the textile casing 200 extend beyond the outer edges of the substrate 300. That is, in the illustrated configuration, the substrate 300 is larger in all radial directions than the substrate 300. As illustrated, an overhanging region 202 is defined as the portion of the textile casing 200 that extends beyond the outer perimeter or radial edges of the curved portions 306 and the end portions 308 of the substrate 300 when the substrate 300 is overlaid over the center of the textile casing 200 in an aligned orientation. That is, the overhanging region 202 is an outer portion of the textile casing 200 that is not overlapped by the substrate 300. As shown in FIGS. 5A and 5B and discussed further below, the overhanging region 202 of the textile casing 200 is configured to be folded over the substrate 300. Therefore, the overhanging region 202 may extend a distance beyond the outer edges of the substrate 300 that is greater than or equal to a combined distance comprising the thickness of the substrate 300 and the width of the curved portions 306 or the end portions 308.

The textile casing 200 has substrate retaining features 220 positioned on the overhanging region 202 between the outer edges of the textile casing 200 and the outer edges of the substrate 300. The substrate retaining features 220 of the textile casing 200 are configured to engage the textile retaining features 320 of the substrate 300. In the illustrated configuration, the substrate retaining features 220 include a plurality of alternating post holes 222 and socket holes 224 that are equidistantly spaced within the overhanging region 202. The post holes 222 and socket holes 224 extend through the thickness of the textile casing 200. The post holes 222 and socket holes 224 may be formed by cutting or punching through the textile casing 200.

As shown in FIGS. 5A and 5B, the plurality of alternating post holes 222 and socket holes 224 of the textile casing 200 are configured to receive the plurality of alternating posts 322 and sockets 324 of the substrate 300 when the overhanging region 202 of the textile casing 200 is folded over the substrate 300. That is, the posts 322 and sockets 324 are inserted and retained in the post holes 222 and socket holes 224 when the overhanging region 202 is folded over the substrate 300. Accordingly, the post holes 222 and socket holes 224 have a corresponding size, shape, order and arrangement as the posts 322 and sockets 324. More specifically, in the illustrated arrangement, the post holes 222 and socket holes 224 are circular which corresponds to the circular cross-sections of the posts 322 and sockets 324. The post holes 222 have a diameter equal to or larger than the outer diameter of the post 322. Similarly, the socket holes 224 have a diameter equal to or larger than the outer diameter of the socket 324. Providing post and socket holes 222, 224 that are significantly larger than the posts 322 and sockets 324 may prevent the posts 322 and sockets 324 from retaining the overhanging region 202 of the textile casing 200 attached to the substrate 300. In some configurations, when the textile casing 200 is formed from an elastic material, the post holes 222 and socket holes 224 may have diameters that are smaller than the diameters of the posts 322 and sockets 324 to provide a friction or interference fit with the substrate 300. The post holes 222 and socket holes 224 are positioned a distance from the outer edge of the substrate 300 within the overhanging portion 202 such that the textile casing 200 is tautly wrapped around the substrate 300 when the post holes 222 and socket holes 224 are connected to the posts 322 and sockets 324. More specifically, in some configurations, the post holes 222 and socket holes 224 are positioned a distance from the outer edge of the substrate 300 that is equal to a combined distance comprising the thickness of the substrate 300 and a distance between the outer edge of the substrate 300 and the centerline that includes the centers of the posts 322 and sockets 324.

Figure 6A:
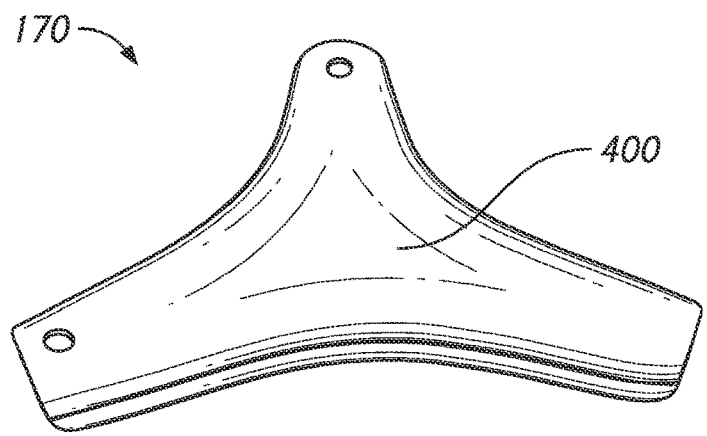
FIG. 6A illustrates a top perspective view of the junction portion formed by connecting a pair of substrates.
Figure 6B:
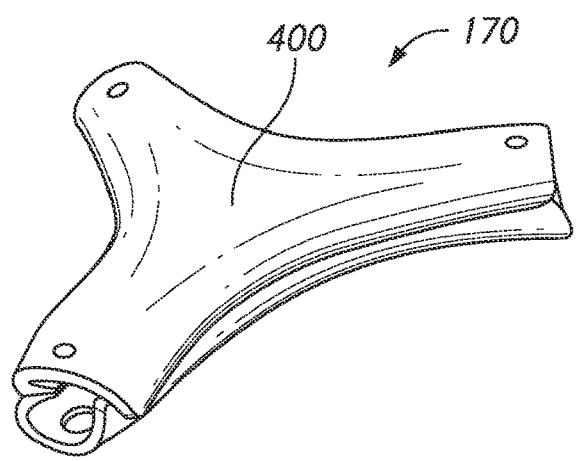
FIG. 6B illustrates a rotated top perspective view of the junction portion formed by connecting a pair of substrates.
Figure 6C:
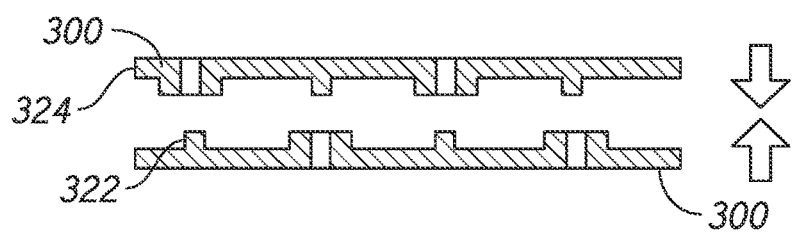
FIG. 6C illustrates a cross-sectional view of a pair of substrates having posts and sockets in alignment.

FIGS. 6A to 6C illustrate a sleeve 400 of the junction portion 170 that is formed by connecting or interlocking the pair of substrates 300. That is, a pair of textile casings 200 is each attached to a substrate 300 via the post and socket holes 222, 224 and the posts 322 and sockets 324. Then, the substrates 300 are attached to each other via the posts 322 and sockets 324 to form the sleeve 400. More specifically, the posts 322 are inserted into and connected to the sockets 324 when connecting one substrate 300 with an adjoining substrate 300 to assemble the junction portion 170, thereby forming a sleeve 400. That is, the posts 322 are positioned in the interior hole 326 of the socket 324 to connect the substrates 300. The snap fit or interference fit between the posts 322 and sockets 324 maintain the posts 322 connected to the sockets 324 and keep the substrates 300 from separating. FIG. 6C illustrates the posts 322 and sockets 324 of a pair of substrates 300 in alignment (without textile casings 200 attached) prior to connecting the posts 322 and sockets 324.

The sleeve 400 of the junction portion 170 is inserted into a cavity of an injection moulding tool (not shown) and the injection moulding tool is closed. When the sleeve 400 is positioned in the mould tool, the textile casings 200 are secured onto the substrate 300 such that the textile casings 200 are prevented and inhibited from moving out of alignment relative to the mould tool and from being pushed out of alignment by the pressure of the injected plastic material. As such, the sleeve 400 allows the plastic core material to be injected into, and to thereby fill, the inside of the sleeve 400. The folded-over edge 230 of the textile casing 200 is permanently fused inside the plastic core material to provide a tidy, smooth and durable edge finish. When the sleeve 400 is injected with the plastic core material, the injected plastic flows through the sleeve 400, fuses with the substrate 300 and bonds with the textile casing 200. The plastic core material can be the same as the material of the substrate 300 such that the plastic core material and the substrate 300 chemically bond resulting in the junction portion 170 having a uniform core. Alternatively, different materials may be used for the substrate 300 and the plastic core material. In some embodiments the plastic core material may be softer or more elastic than the substrate 300. This may provide additional flexibility and elasticity for improving fitment of the headgear, and may also improve comfort for the user.

Figure 7A:
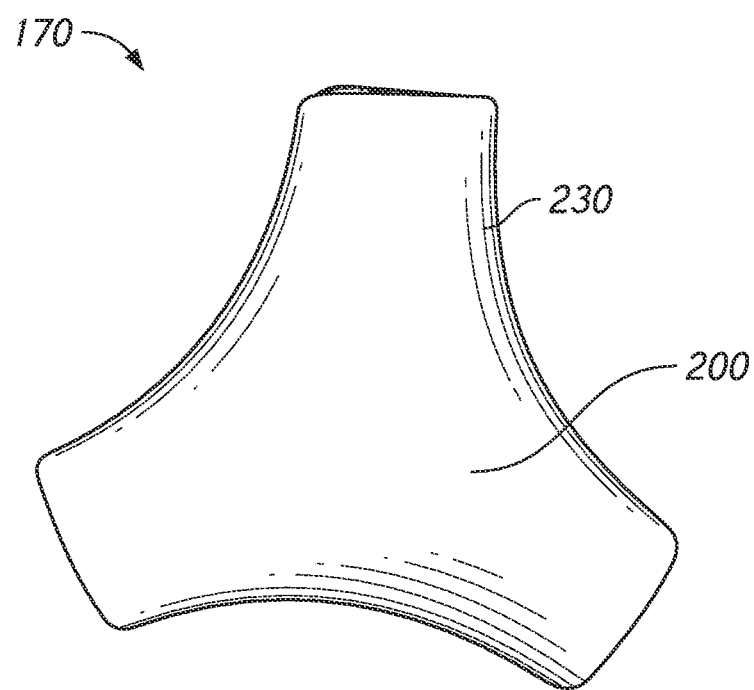
FIG. 7A illustrates a top view of the junction portion formed by the intra-moulding arrangement of the present disclosure.
Figure 7B:
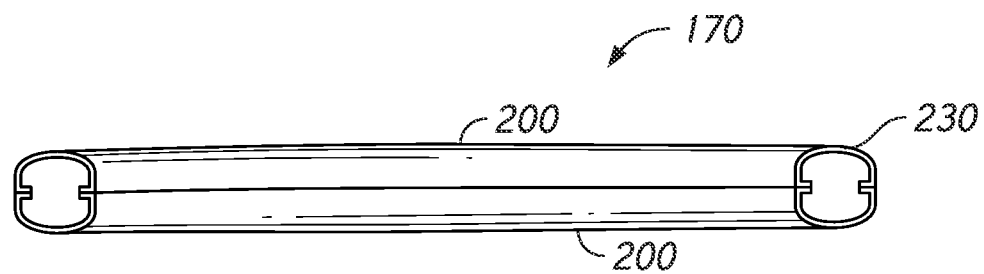
FIG. 7B illustrates a side profile view of the junction portion formed by the intra-moulding arrangement of the present disclosure.

FIGS. 7A and 7B show the junction portion 170 after being injected with plastic core material and allowed to cool. As shown, the folding over of the textile casing 200 onto the substrate 300 produces an edge finish that is both aesthetically pleasing and comfortable against a user's head. That is, with the folded-over edges 230 of the textile casing 200 provide a smoother edge that is comfortable against the user's skin. In contrast, a junction portion 170 formed having crimped edges of the textile casings that extend radially outward from the junction portion 170 (i.e., as opposed to being folded inward into the junction portion 170) may have an edge finish that is untidy in appearance with sharp edges if injected plastic core material protrudes from the edges of the textile casings (i.e., flash). However, folding the overhanging region 202 of the textile casing 200 over and onto the substrate 300 provides the junction portion 170 with a smooth contoured edge that follows the shape of the substrate 300.

In some embodiments, only one substrate 300 may have a textile casing 200 such that only one side of the junction portion 170 has a textile casing. Similarly, the first and second textile casings 200 may be made from differing materials. This may provide the headgear 100 with varied physical properties in different regions of the headgear 100. Further the height of the posts 322 and sockets 324 may vary according to the thickness of the textile casing 200. The heights of the posts 322 may also be different from the heights of the sockets 324. Similarly, the number or quantity of posts 322 and sockets 324 and the spacing between the posts 322 and sockets 324 may vary according to the size and shape of the junction portion 170 and/or the flexibility of the textile casing 200. Further, the posts 322 and sockets 324 are not limited to having circular cross-sectional shapes. In some configurations, the posts 322 and sockets 324 may have a variety of cross-sectional shapes such as, for example, polygonal and/or curved elongate shapes. Further, the posts 322 and sockets 324 may have cross-sectional shapes that are configured to reduce the formation of wrinkles or creases of the textile casing 200 when the textile casing 200 is folded over a curved portion of the substrate 300. Reducing wrinkling or creasing provides a cleaner edge finish that is more aesthetically pleasing and comfortable against a user's head. Further, it should be understood to one of ordinary skill in the art that the above described intra-moulding arrangement is not limited to the forming of junction portions of the headgear. The above described intra-moulding arrangement may be used to form any portion of the headgear to improve manufacturing reliability and provide an edge finish that is both aesthetically pleasing and comfortable against a user's head.

Figure 8:
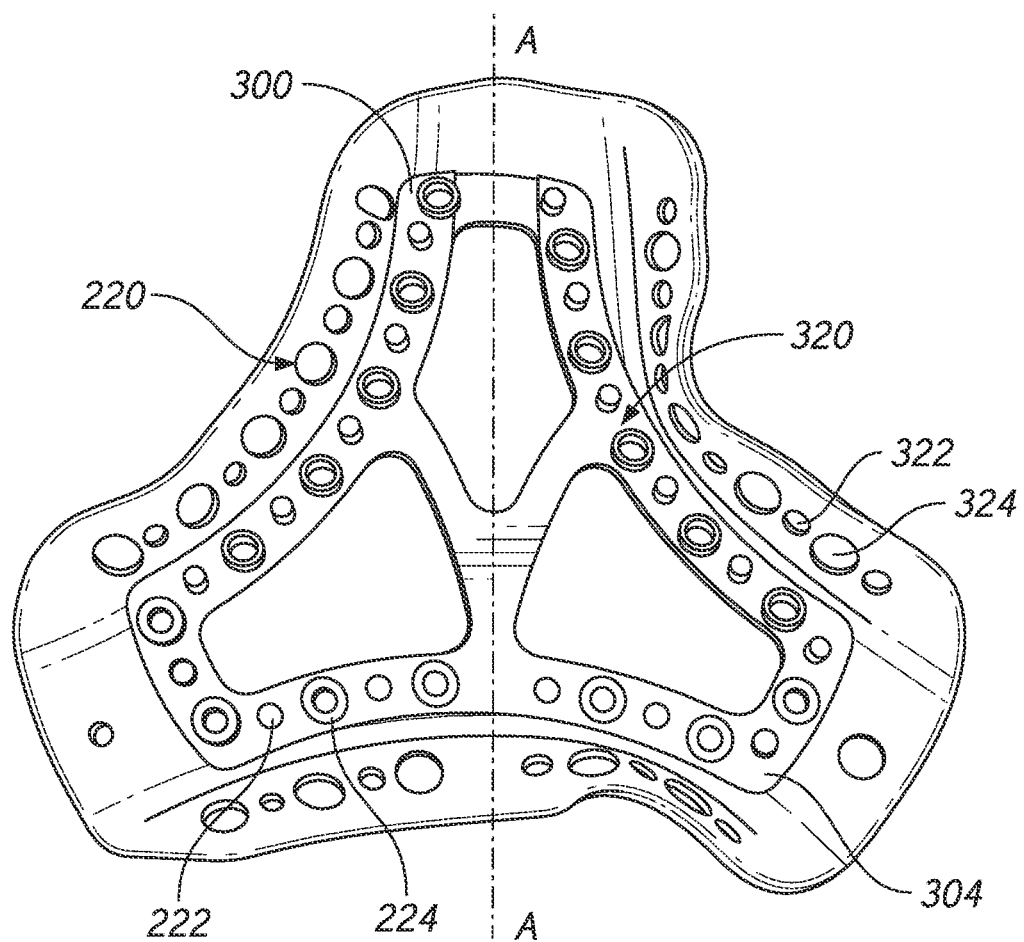
FIG. 8 illustrates a top view of an alternative reversible or modular substrate arrangement.

FIG. 8 illustrates a reversible substrate configuration having posts 322 and sockets 324 that alternate along each edge of the substrate 300 such that only a single substrate configuration is required. That is, the substrates 300 are reversible such that a pair of substrates 300 can be joined or interlocked together when the inner surfaces 302 of each substrate 300 face each other. The posts 322 and sockets 324 are arranged such that each substrate 300 of an adjoining substrate pair is identical. More specifically, the posts 322 and sockets 324 alternate along each edge of the substrate 300 and each post 322 opposes a socket 324 on either side of a central plane marked as A-A in FIG. 8. The textile casing 200 has post holes 222 and socket holes 224 that correspond with the posts 322 and sockets 324. This arrangement allows a pair of identical textile casings 200 and substrates 300 to be connected together which minimises components and manufacturing costs.

Figure 9:
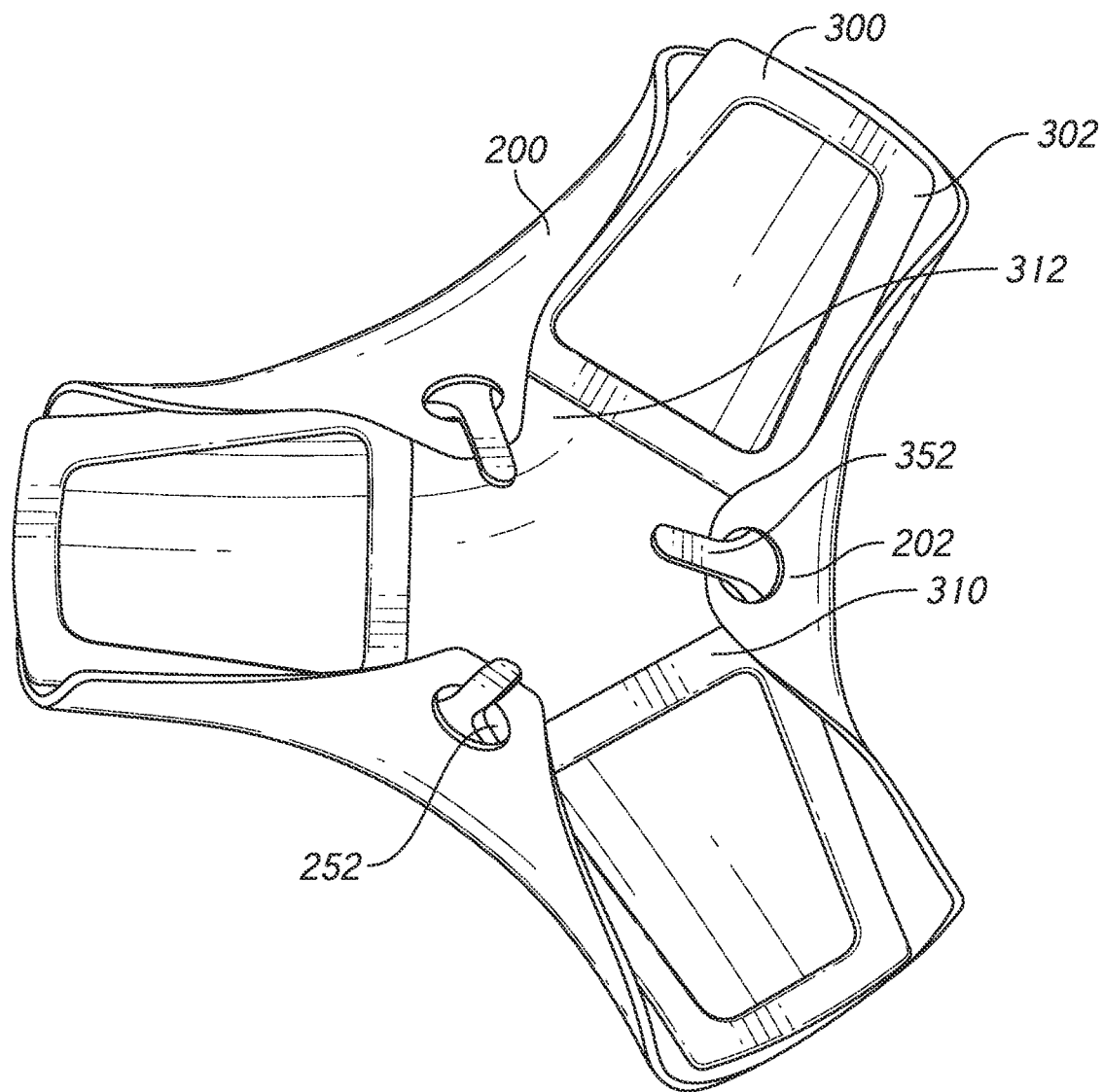
FIG. 9 illustrates a top view of an alternative substrate arrangement having a hook for retaining the textile casing.

FIG. 9 illustrates an alternative retaining features configuration having a substrate 300 with retaining hooks 352 that are inserted through a corresponding hole 252 on the overhanging region 202 of the textile casing 200 to retain and lock the textile casing 200 onto the substrate 300. The retaining hooks 352 extend toward a centre of the substrate 300. The crossbars 310 are positioned on each side of the retaining hooks 352 and extend to connect adjacent curved portions 306. In this embodiment there are no retaining features such as posts and sockets to secure two substrates together which allow the substrate 300 to be thinner and narrower. The retaining hooks 352 sit within apertures 312 such that the retaining hooks are flush with the substrate 300 which reduces the overall thickness of the substrate 300 and the headgear. That is, the curved and end portions 306, 308 and the retaining hooks 352 are planar. Further, the substrates 300 may be placed on top of each other (i.e., back-to-back with the inner surfaces 302 facing each other) within the cavity of the injection moulding tool to form a sleeve within which plastic core material is injected. In alternative embodiments, the textile casing may be attached to the substrate by any other appropriate means including adhesives or welding, rather than a mechanical bond.

Figure 10A:
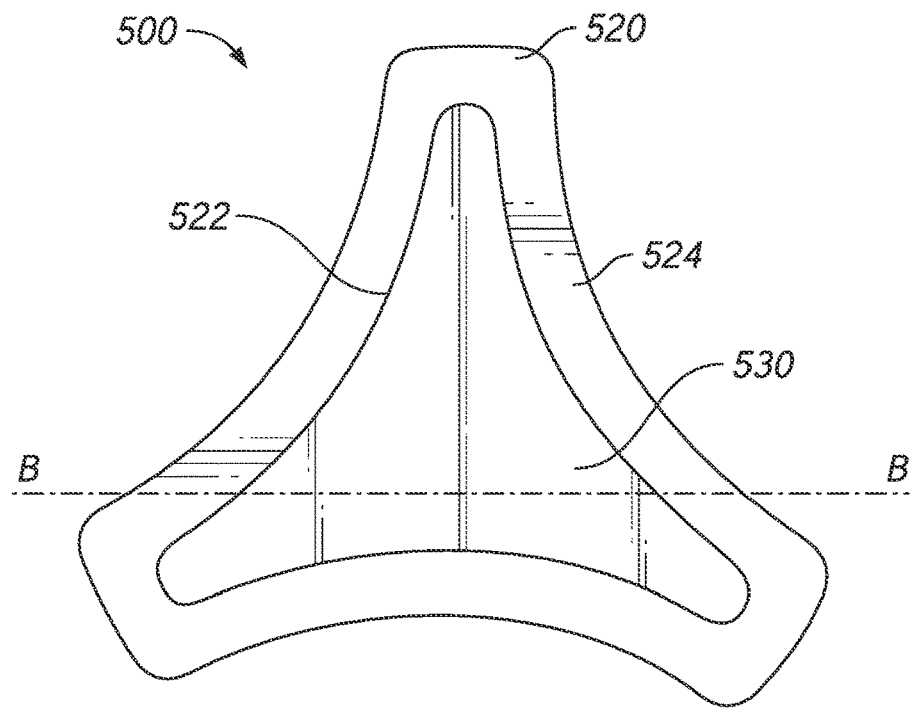
FIG. 10A illustrates a top view of an alternative substrate arrangement having an insert within an aperture of the substrate.
Figure 10B:
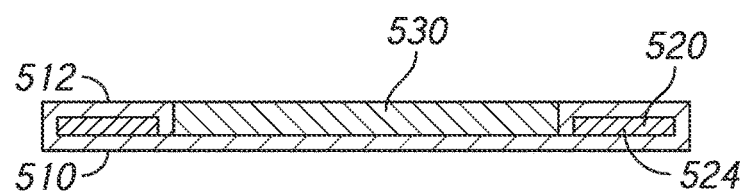
FIG. 10B illustrates a cross-sectional view of the alternative substrate arrangement along a line B-B of FIG. 10A having an insert positioned within the aperture of the substrate.

FIGS. 10A and 10B illustrates an alternative substrate arrangement for forming a junction portion 500 without having retaining features formed on the substrate. The junction portion 500 includes a textile casing 510, a substrate 520 and an insert 530. Similar to the substrate arrangements described above, the substrate 520 provides a frame structure that the textile casing 200 is wrapped over and secured onto. Also, the substrate 520 has an aperture 522 defined by an outer frame 524. However, in contrast to latching the overhanging region 512 of the textile casing 510 onto posts and sockets, the overhanging region 512 is folded over the edges of the outer frame 524 such that the overhanging region 512 extends into the aperture 522. The insert 530 is then inserted into the aperture 522 so that the edges of the overhanging region 512 are sandwiched between the insert 530 and the outer frame 524, as shown in FIG. 10B. Accordingly, a pair of textile covered substrates 520 may be placed be placed on top of each other (i.e., back-to-back with the inserts 530 facing each other) within the cavity of the injection moulding tool to form a sleeve within which plastic core material is injected.

Figure 10C:
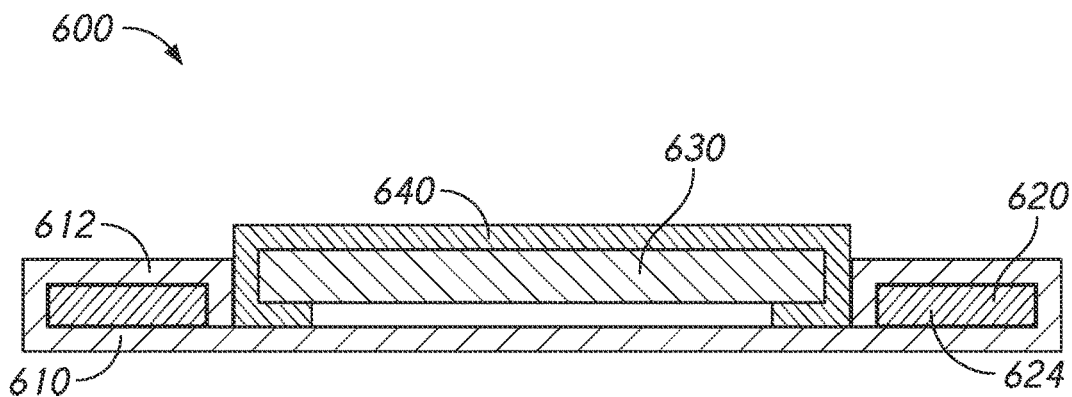
FIG. 10C illustrates a cross-sectional view of an alternative substrate arrangement along a line B-B of FIG. 10A having a textile covered insert positioned within the aperture of the substrate.

FIG. 10C illustrates a substrate arrangement having an insert 630 covered by a textile casing 640 for forming a textile-covered junction portion 600 using a single substrate 620 for providing a thinner junction portion 600 and headgear. The insert 630 is pushed into the aperture 622 defined by the outer frame 624 of the substrate 620. However, in contrast to the junction portion 500 in FIGS. 10A-B, the edges of the overhanging region 612 and the edges of the textile casing 640 are sandwiched between the insert 630 and the outer frame 624. Accordingly, the junction portion 600 may be entirely covered in textile material without utilizing a pair of substrates 620 which provides a thinner overall headgear. A thinner headgear is beneficial to user comfort and the desirability of the product. Further, in contrast to a junction formed using a pair of substrates, the seam between textile casings 610, 640 is positioned away from the peripheral edges of the junction portion 600, which provides a softer and more aesthetically pleasing appearance to the junction. In some configurations, different textiles may be used to cover the substrate 620 and the insert 630.

Figure 11:
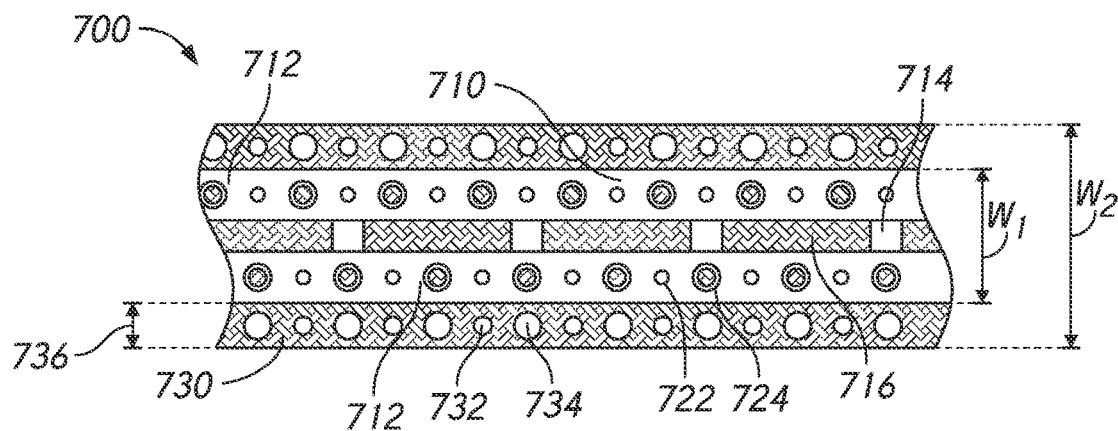
FIG. 11 illustrates a top view of an alternative substrate arrangement for forming a headgear strap.

FIG. 11 illustrates a substrate arrangement for forming an elongate headgear strap 700. In contrast to the junction portion 170 in FIGS. 2A-7B, the strap 700 comprises a single substrate 710 that is wrapped in a single textile casing 730. The substrate 710 is folded over onto itself to form a sleeve within which plastic core material is injected. The substrate 710 includes a pair of edge segments 712 that extend and span the length of the strap 700. The edge segments 712 are connected by a plurality of crossbars 714 that link the edge segments 712 and provide stability and structure between the edge segments 712. The crossbars 714 may be thinner in thickness than the edge segments 712 such that the crossbars 714 are more flexible to allow the substrate 710 to be folded over onto itself. The crossbars 714 may be equidistantly spaced along a gap 716 that separates the edge segments 712.

The edge segments 712 have sockets 722 and posts 724 that are equidistantly spaced along the edge segments 712. To allow the edge segments 712 to be folded over onto itself and connected, the order of the posts 722 and sockets 724 on one of the edge segments 712 is inversed, reversed or offset such that a socket 724 on one edge segment 712 is positioned adjacent to a post 722 on the adjoining segment 712 (i.e., in contrast to having two opposing posts 722 or two opposing sockets 724). Put another way, the adjoining edge segment 712 may have an opposite pattern of posts 722 and sockets 724 such that the posts 722 of the adjoining edge segment 712 align with the sockets 724 of the other substrate, and vice versa. In some configurations (not shown), one edge segment 712 may have only posts 722 while the adjoining edge segment 712 has only sockets 724.

The textile casing 730 has a corresponding shape as the substrate 710. The textile casing 730 includes an overhanging region 736 that extends beyond the edges of the substrate 710 and is not overlapped by the substrate 710. As illustrated, the substrate 710 has a substrate width W1 that is measured perpendicular to the lengthwise direction of the strap 700. The textile casing 730 has a textile casing width W2 this is also measure perpendicular to the lengthwise direction of the strap 700. The textile casing width W2 is greater than the substrate width W1. The remainder of non-overlapping textile casing 730 is illustrated as overhanging regions 736. The substrate 710 is positioned in an overlapping orientation with the textile casing 730 such that overhanging regions 736 are positioned on both sides of the substrate 710. The overhanging region 736 of the textile casing 730 includes post holes 732 and socket holes 734 through which the sockets 722 and posts 724 are positioned therein to retain and lock the textile casing 730 onto the substrate 710 when the overhanging regions 736 are folded over the substrate 710. When the textile casing 730 is attached to the substrate 710, the substrate 710 is folded over onto itself and the edge segments 712 are connected via the posts 722 and sockets 724 which forms a sleeve within which plastic core material is injected.

Figures 12A, 12B:
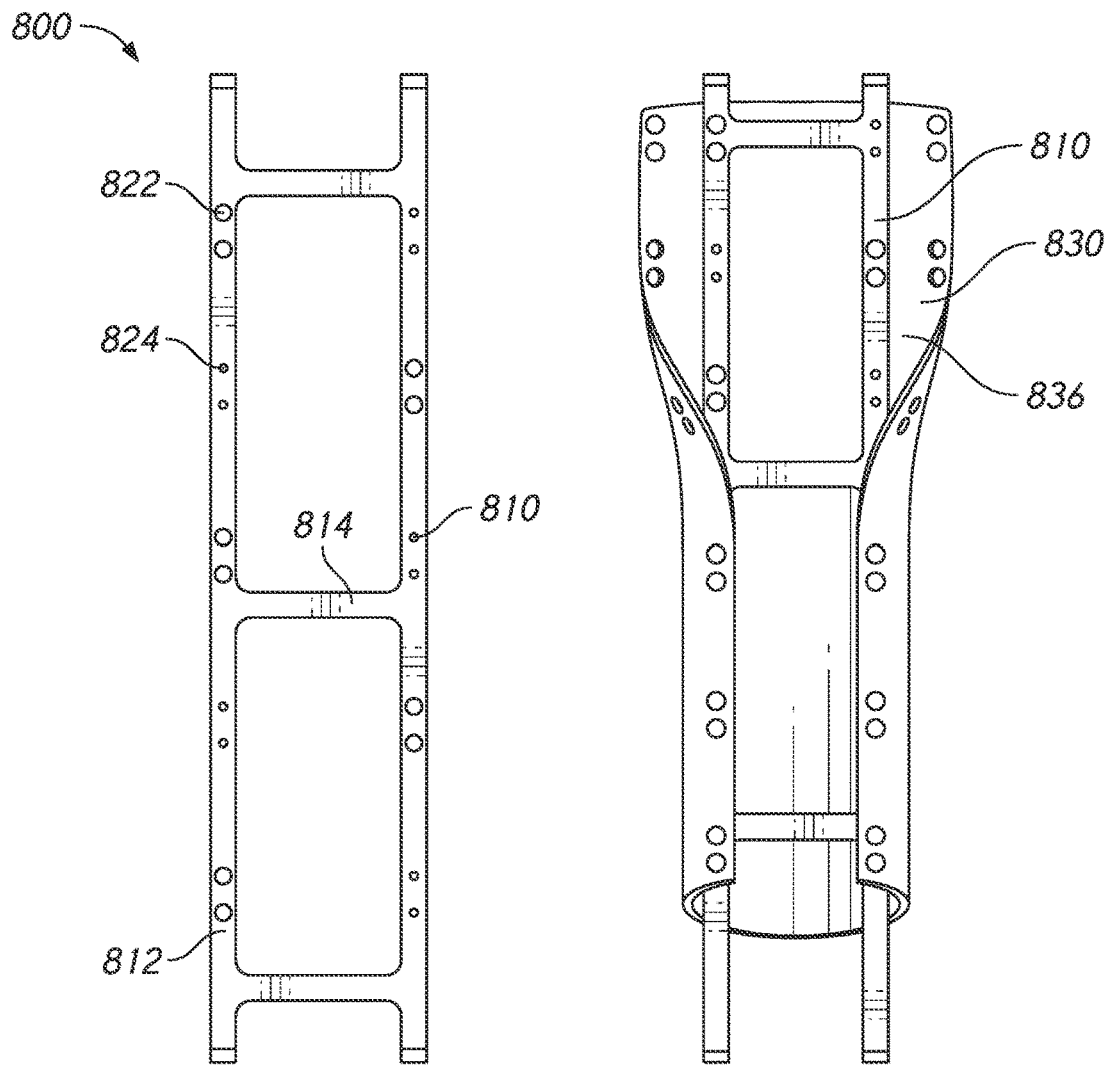
FIG. 12A illustrates a top view of an alternative substrate arrangement for forming a headgear strap having an alternative post and socket arrangement.
FIG. 12B illustrates a top view of the alternative substrate arrangement in FIG. 12A having a textile casing applied to a substrate.
Figure 12C:
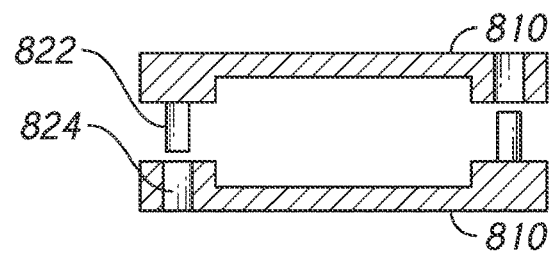
FIG. 12C illustrates a cross-sectional view of the substrate in FIG. 12A.
Figure 12D:
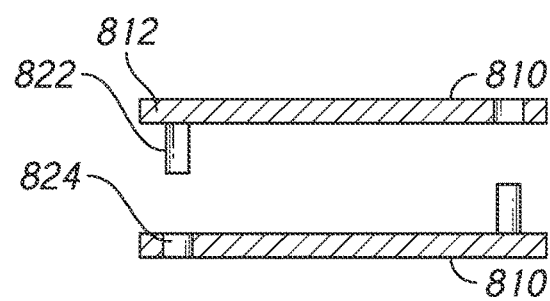
FIG. 12D illustrates a cross-sectional view of the substrate in FIG. 12A having edge rails and crossbars with a uniform thickness.

FIGS. 12A to 12F illustrates an alternative substrate arrangement for forming an elongate headgear strap 800. Similar to the junction portion 170 in FIGS. 2A-7B, the strap 800 comprises a pair of substrates 810 that extend and span the length of the strap 800 and are wrapped in a textile casing 830, as shown in FIG. 12B. The segments 812 are connected by a plurality of crossbars 814 that link the edge segments 812 and provide stability and structure between the edge segments 812. In contrast to the substrate 710 in FIG. 11, the crossbars 814 are substantially rigid. As illustrated in FIG. 12C, the edge segments 812 may have a thinner thickness than the crossbars 814 to provide longitudinal strength along the length of the strap 800. Alternatively, the edge segments 812 and the crossbars 814 may be identical in thickness, as shown in FIG. 12D.

The edge segments 812 have sockets 822 and posts 824 that are spaced along the edge segments 812. In contrast to the arrangement of sockets and posts 122, 124 in FIGS. 2A-7B, the sockets and posts 822, 824 are arranged in alternating pairs that are equidistantly spaced along the length of the segments 812. The arrangement of sockets and posts 822, 824 are inversed, reversed or offset such that a socket 824 on one edge segment 812 is positioned adjacent to a post 822 on the adjoining segment 812. As a result, in some configurations, the substrate 810 may be modular such that a pair of identical substrates 810 may be connected together which minimises components and manufacturing costs. It should be understood to one of ordinary skill in the art that the strap 800 is not limited to the illustrated positioning, order and/or arrangement of sockets and posts 822, 824. For example, the arrangement of sockets and posts 822, 824 may vary depending on, the shape or length of strap, the flexibility of the textile casing, the strength of the substrate, etc.

Figure 12E:
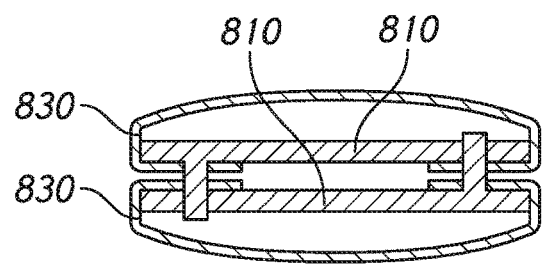
FIG. 12E illustrates a cross-sectional view of the alternative substrate arrangement in FIG. 12A prior to intra-moulding.
Figure 12F:
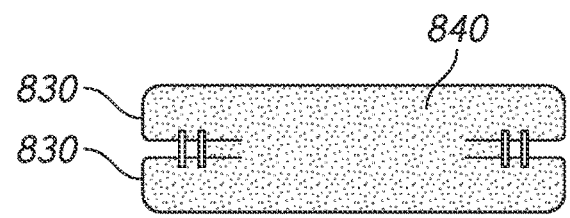
FIG. 12F illustrates a cross-sectional view of the alternative substrate arrangement in FIG. 12A after intra-moulding.

The textile casing 830 has a corresponding shape as the substrate 810 and includes an overhanging region 836 that extends beyond the edges of the substrate 810 and is not overlapped by the substrate 810. The overhanging region 836 of the textile casing 830 includes post holes 832 and socket holes 834 through which the sockets 822 and posts 824 are positioned therein to retain the textile casing 830 onto the substrate 810 when the overhanging regions 836 are folded over the substrate 810 and lock the textile casing 830 when the substrates 810 are connected. When the textile casing 830 is attached to the substrate 810, a pair of substrates 810 is interlocked by inserting the posts 822 into the sockets 824, as shown in FIG. 12E. Accordingly, the interlocking substrates 810 form a sleeve within which plastic core material is injected. FIG. 12F illustrates a cross-section of the strap 800 after the plastic core material is injected and intra-moulding is completed. As shown, the substrate 810 and the plastic core material form a uniform core 840. That is, the substrates 810 and the plastic core material chemically bond and combine to form the uniform core 840.

Figure 13:
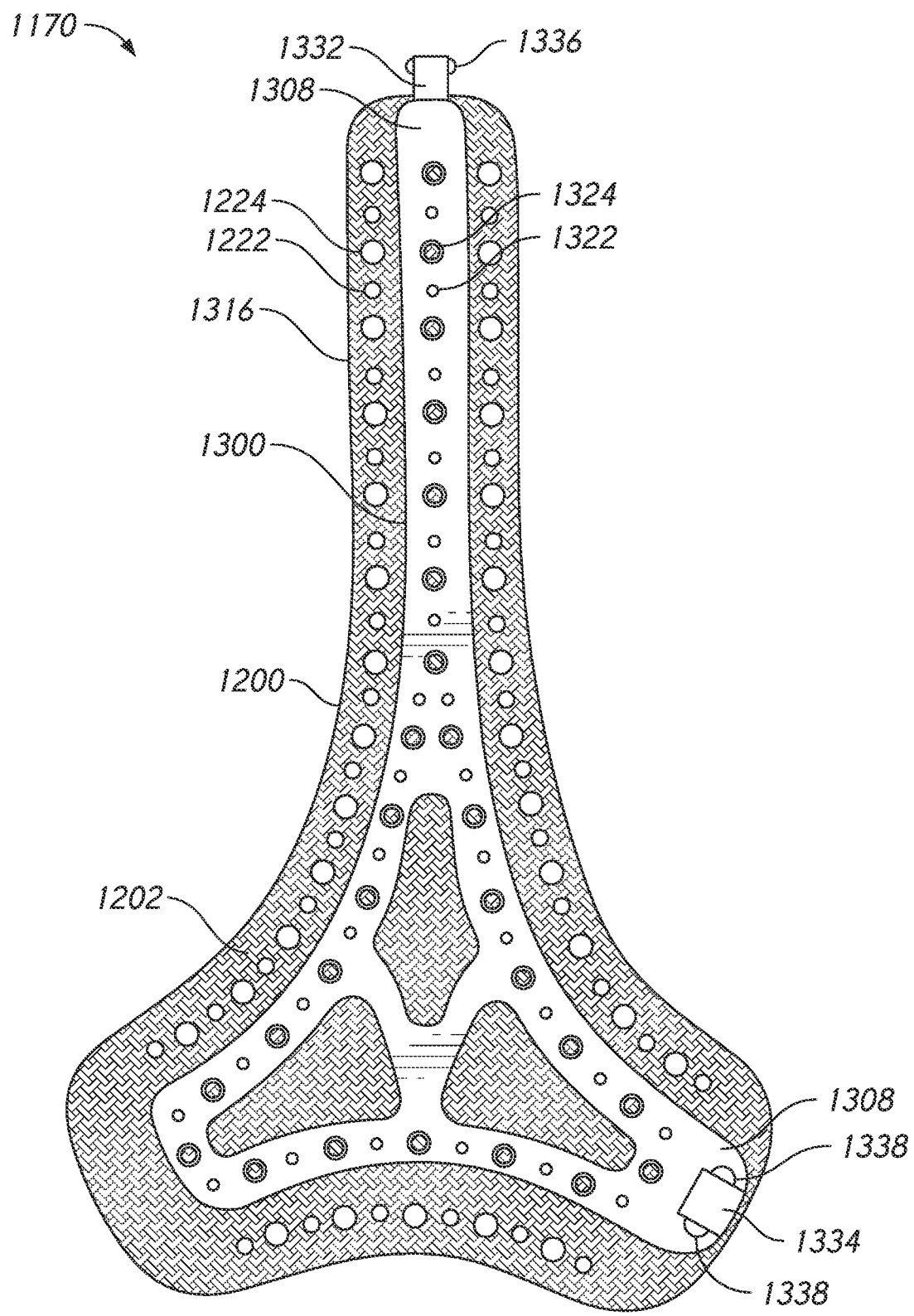
FIG. 13 illustrates a top view of an alternative substrate arrangement having connectors preformed into the substrate.

FIG. 13 illustrates a substrate arrangement having one or more headgear straps and/or connectors that are integrally formed with a junction portion 1170. The junction portion 1170 comprises a pair of substrates 1300 that are wrapped in textile casings 1200. Similar to the junction portion 170 in FIGS. 2A-7B, the pair of textile-wrapped substrates 1300 is connected to form a sleeve within which plastic core material is injected. The junction portion 1170 is formed by connecting the pair of textile-wrapped substrate 1300 wrapped. However, in contrast, the substrate 1300 includes a strap portion 1316 extending from one end of the substrate 1300. The strap portion 1316 includes posts 1322 and sockets 1324 that are equidistantly spaced along the length of the strap portion 1316. Similarly, the textile casing 1200 has a corresponding shape as the substrate 1300 to accommodate the strap portion 1316 such that the textile casing 1200 may be wrapped around the strap portion 1316. The textile casing 1200 includes an overhanging region 1202 that extends beyond and is not overlapped by the substrate 1300. The strap portion 1316 includes post holes 1222 and socket holes 1224 through which the posts 1322 and sockets 1324 are positioned therein to retain the overhanging region 1202 of the textile casing 1200 when the textile casing 1200 is folded over the substrate 1300.

The substrate 1300 includes male and female connectors 1332, 1334 attached to end portions 1308 of the substrate 1300. The male and female connectors 1332, 1334 may be used to secure the headgear to the respiratory mask and provide size and fitment adjustability to the headgear. The male and female connectors 1332, 1334 may be integrally pre-formed into the substrate 1300. Alternatively, the male and female connectors 1332, 1334 may be integrally formed during the intra-moulding process. As illustrated, the male connector 1332 includes bumps 1336 that protrude outward from the male connector 1332 and the female connector 1334 includes notches 1338 notches recessed into the female connector 1334 to provide a push-fit or snap-fit connection with opposing male and female connectors 1332, 1334 (e.g., male and female connectors on the mask frame, a separate strap, the opposite junction, etc.). That is, the male connector 1332 is connected to the female connector 1334 by inserting the male connector 1332 into the female connector 1334 such that the bumps 1336 are positioned within the notches 1338. The male connector 1332 extends beyond the textile casing 1200 such that the textile casing 1200 does not obstruct insertion of the male connector 1332 into the female connector 1334. Similarly, the opening of the female connector 1334 may extend from the end portion 1308 of the substrate 1300 and be aligned with the edge of the textile casing 1200 such that the textile casing 1200 does not obstruct insertion of the male connector 1332 into the female connector 1334. It should be understood to one of ordinary skill in the art that the junction portion 1170 is not limited to male and female snap-fit connectors and may include alternative connection arrangements. It should be understood to one of ordinary skill in the art that the male and female connectors 1332, 1334 may be combined with other substrate configurations discussed herein.

Figure 14:
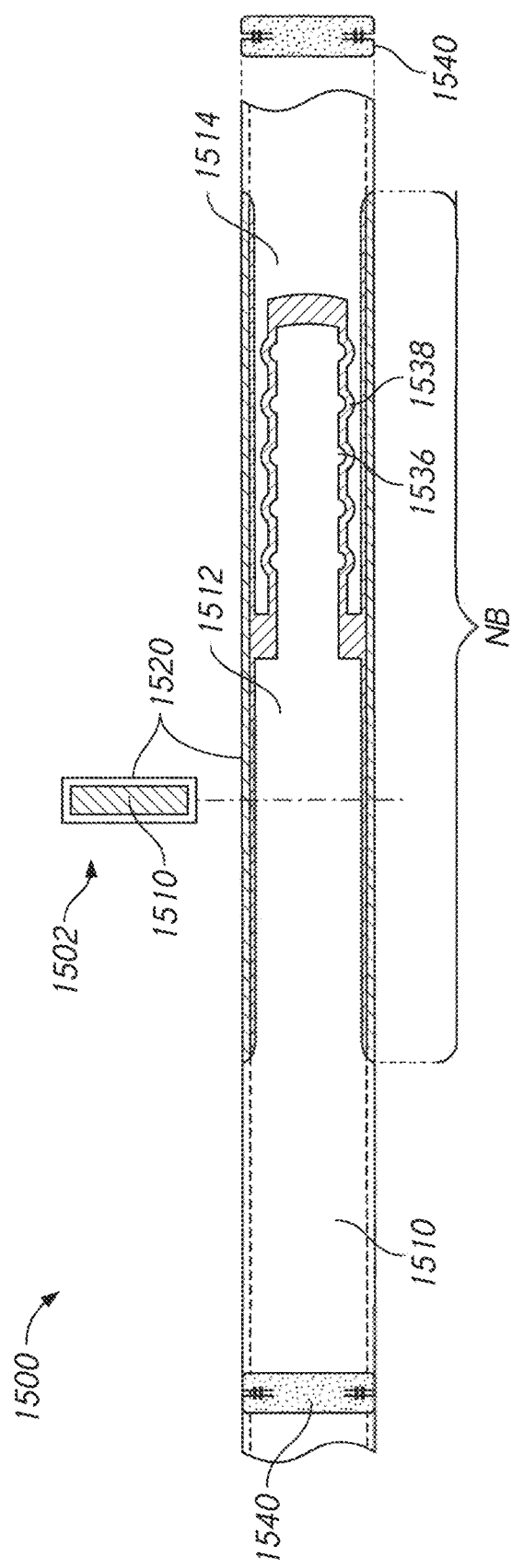
FIG. 14 illustrates a top view of an alternative substrate arrangement for forming a strap of a headgear having an integrally formed length adjustment mechanism.

FIG. 14 illustrates a substrate configuration for a strap 1500 having an integrally formed internal length adjustment mechanism 1502. The length adjustment mechanism 1502 may be integrally formed internally within a headgear strap which provides a strap and adjustment mechanism arrangement with a tidy aesthetic appearance. Similar to the above configurations, the length adjustment mechanism includes substrates 1510 that are wrapped in textile casings 1520. The textile casings 1520 may be attached to the substrates 1510 using any of the features or combination of features described above such that the ends of the textile casings 1520 are folded into and bonded with the core, as illustrated. Similarly, the substrates 1510 may include a single substrate or an interlocking pair of substrates, as previously described herein.

The substrates 1510 have a male substrate portion 1512 and a female substrate portion 1514 that are integrally formed into the substrate 1510. The male substrate portion 1512 is engaged with the female substrate portion 1514 to provide length adjustability to the strap 1500. The male substrate portion 1512 has bumps 1536 that protrude outward from the male substrate portion 1512 in a direction perpendicular to a lengthwise direction of the strap 1500 and towards the female substrate portion 1514. The female substrate portion 1514 has notches 1538 recessed into the female substrate portion 1514 and having a shape that corresponds to the shape of the bumps 1536. The bumps 1536 engage the notches 1538 via a snap-fit to allow the adjustment mechanism 1502 to provide discrete length adjustment of the strap 1500. The substrates 1510 are pre-molded with the male substrate portion 1512 and a female substrate portion 1514.

As illustrated in the cross-sectional views, the textile casing 1520 surrounding portions of the strap 1500 containing the length adjustment mechanism 1502 is not bonded to the substrate 1510, which is designated in FIG. 14 as a non-bonded region NB. However, portions of textile casing 1520 outside of the non-bonded region NB are bonded to the substrate 1510 such that the strap 1500 has a uniform core 1540, as shown in the cutaway cross-sectional view. The textile casing 1520 is not bonded within the non-bonded region NB such that the textile casing 1520 is free to expand and contract when the length adjustment mechanism 1502 is adjusted (i.e., the relative positions of the male substrate portion 1512 and a female substrate portion 1514 changes such that the strap 1500 increases or decreases in length). Accordingly, the textile casing 1520 may be formed from a stretchable elastic material such as Breath-o-Prene™.

Figure 15:
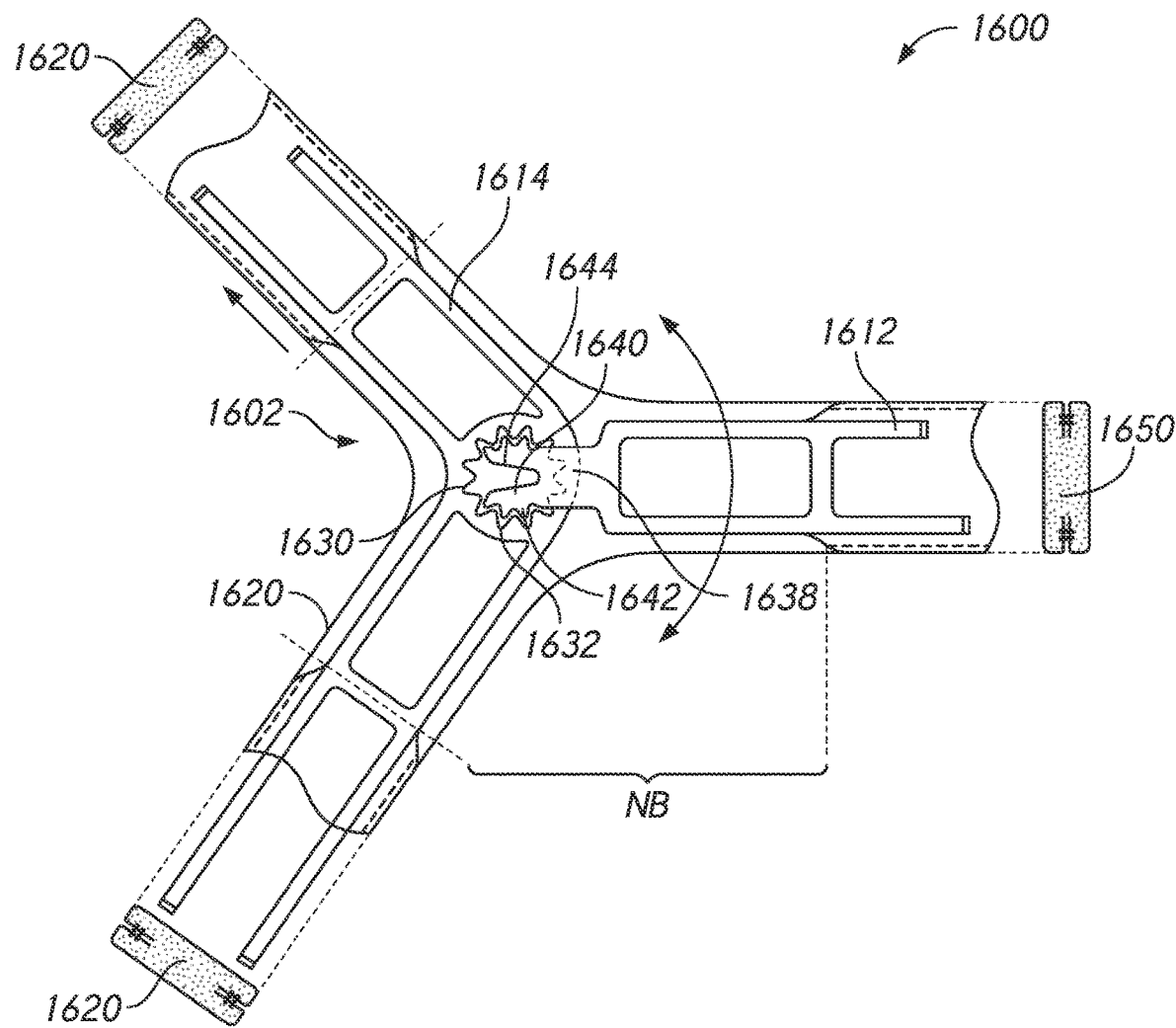
FIG. 15 illustrates a top view of an alternative substrate arrangement for forming a junction portion of a headgear having an integrally formed angular adjustment mechanism.

FIG. 15 illustrates a substrate configuration for a junction portion 1600 having an integrally formed internal angular adjustment mechanism 1602. The angular adjustment mechanism 1602 allows the angle between headgear straps to be adjustable which provides improved fitment for a range of user head shapes and sizes. Similar to the above configurations, the angular adjustment mechanism includes substrates 1610 that are wrapped in textile casings 1620. Further, the textile casing 1620 surrounding portions of the junction portion 1600 containing the angular adjustment mechanism 1602 are not bonded to the substrate 1610, which are designated in FIG. 15 as a non-bonded regions NB. Similarly, portions of the textile casings 1620 outside of the non-bonded region NB are bonded to the substrate 1610 such that the junction portion 1600 has a uniform core 1650, as shown in the cutaway cross-sectional views.

The substrates 1610 have a male substrate portion 1612 and a female substrate portion 1614 that are integrally formed into the substrate 1610. The male substrate portion 1612 is engaged with the female substrate portion 1614 to provide rotational adjustability to the junction portion 1600. The female substrate portion 1612 has an internal spur gear 1630 having a plurality of teeth 1632. The male substrate portion 1612 has a pinion gear 1640 positioned on an arm 1638 that extends from an end portion of male substrate portion 1612. The arm 1638 and the pinion gear 1640 are integrally formed with the male substrate portion 1612. The pinion gear 1640 has a plurality of teeth 1642 arranged around on an outer circumference of the pinion gear 1640. The teeth 1642 of the pinion gear 1640 are engaged with the teeth 1632 of the internal spur gear 1630 to maintain the relative rotational position between the male substrate portion 1612 and the female substrate portion 1614. The pinion gear 1640 is forked, having a centrally located split or fork 1644 that is parallel to the length of the arm 1638. The fork 1644 allows the two sides of the pinion gear 1640 to flex towards each other, which reduces the diameter of the pinion gear 1640 to allow the teeth 1632, 1642 of the internal spur gear 1630 and the pinion gear 1640 to disengage. While disengaged, the teeth 1632, 1642 pass each other which allow the male substrate portion 1612 to be rotated relative to the female substrate portion 1614 such that the angle between headgear straps can be adjusted which provides improved fitment for a range of user head shapes and sizes.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A junction portion in a headgear assembly at which two or more straps of the headgear assembly connect, the junction portion comprising:
    a first substrate;
    a second substrate attached to the first substrate;
    a first textile casing attached to the first substrate;
    a second textile casing attached to the second substrate; and
    a plastic core that is surrounded by the first and second textile casings and is bonded to the first and second substrates and the first and second textile casings,
    wherein each of the first and second substrates include a first retaining structure,
    wherein each of the first and second textile casings include a second retaining structure, and
    wherein the first and second retaining structures are configured to engage each other to attach the first textile casing onto the first substrate and the second textile casing onto the second substrate.

2. The junction portion of claim 1, wherein the first textile casing covers an inwardly-facing surface of the headgear assembly and the second textile casing covers an outwardly-facing surface of the headgear assembly.

3. The junction portion of claim 1, wherein ends of the first and second textile casing are positioned between the first and second substrates.

4. The junction portion of claim 1, wherein the first retaining structure of the first substrate engages the first retaining structure of the second substrate to connect the first and second substrates.

5. The junction portion of claim 1, wherein the first retaining structure includes a post protruding outward from a surface of at least one of the first and second substrates, and a socket positioned on at least an other of the first and second substrates, the socket having an inner hole, wherein the post is positioned within the inner hole to connect the first and second substrates.

6. The junction portion of claim 5, wherein the socket protrudes outward from a surface of the other of the first and second substrates.

7. The junction portion of claim 5, wherein the second retaining structure includes at least one hole extending through each of the first and second textile casings, wherein at least one of the post and the socket engages the hole to attach the first textile casing on the first substrate and the second textile casing on the second substrate.

8. The junction portion of claim 1, wherein the second retaining structure is positioned on portions of the first and second textile casing that are positioned between the first and second substrates.

9. The junction portion of claim 1, further comprising:
a strap connector preformed in at least one of the first and second substrates.

10. The junction portion of claim 1, further comprising:
a length adjustment mechanism preformed in at least one of the first and second substrates.

11. The junction portion of claim 1, further comprising:
an angular adjustment mechanism preformed in at least one of the first and second substrates.

12. The junction portion of claim 1, wherein at least one of the first and second substrates includes a gate.

13. The junction portion of claim 1, wherein the first and second substrates are identical.

14. The junction portion of claim 1, wherein the plastic core comprises an injection moulded plastic material that is injected between the first and second textile casings.

* * * * *